US012758797B2

(12) United States Patent
Sun et al.

(10) Patent No.: US 12,758,797 B2
(45) Date of Patent: Oct. 13, 2026

(54) METHOD AND APPARATUS FOR CONTROLLING RADIOTHERAPY EQUIPMENT, DEVICE, AND STORAGE MEDIUM

(71) Applicant: OUR UNITED CORPORATION, Xi'an (CN)

(72) Inventors: Bing Sun, Xi'an (CN); Shifeng Fan, Xi'an (CN)

(73) Assignee: OUR UNITED CORPORATION, Xi'an (CN)

( * ) Notice: Subject to any disclaimer, the term of this patent is extended or adjusted under 35 U.S.C. 154(b) by 174 days.

(21) Appl. No.: 18/721,765

(22) PCT Filed: Dec. 20, 2021

(86) PCT No.: PCT/CN2021/139698
§ 371 (c)(1),
(2) Date: Jun. 19, 2024

(87) PCT Pub. No.: WO2023/115261
PCT Pub. Date: Jun. 29, 2023

(65) Prior Publication Data

US 2025/0256129 A1 Aug. 14, 2025

(51) Int. Cl.
*A61N 5/10* (2006.01)
*G16H 20/40* (2018.01)

(52) U.S. Cl.
CPC .......... *A61N 5/1065* (2013.01); *G16H 20/40* (2018.01); *A61N 2005/1074* (2013.01)

(58) Field of Classification Search
CPC .......... A61N 5/1065; A61N 2005/1074; A61N 5/103; A61N 5/10; G16H 20/40; G16H 40/20; A61B 6/03
See application file for complete search history.

(56) References Cited

U.S. PATENT DOCUMENTS

2021/0252309 A1 8/2021 Yan et al.

FOREIGN PATENT DOCUMENTS

CN 104338240 A 2/2015
CN 107358607 A 11/2017
(Continued)

OTHER PUBLICATIONS

International Search Report and Written Opinion of the International Searching Authority from the European Patent Office, in PCT/CN2021/139698 dated Aug. 8, 2022, which is an international application to which this application claims priority.

*Primary Examiner* — Kiho Kim
(74) *Attorney, Agent, or Firm* — Kolitch Romano Dascenzo Gates LLP

(57) ABSTRACT

Provided is a method for controlling radiotherapy equipment. A plurality of target treatment plans for a target object are acquired, wherein the plurality of target treatment plans include a treatment plan for the focused treatment head and a treatment plan for the conformal treatment head; an examination on the plurality of target treatment plans is performed; and in a case that the plurality of target treatment plans pass the examination, the focused treatment head is controlled to execute the treatment plan for the focused treatment head and the conformal treatment head is controlled to execute the treatment plan for the conformal treatment head.

18 Claims, 4 Drawing Sheets

(56) References Cited

FOREIGN PATENT DOCUMENTS

| | | | | |
|---|---|---|---|---|
| CN | 107480416 | A | 12/2017 | |
| CN | 113573776 | A | 10/2021 | |
| JP | 2011000301 | A | 1/2011 | |
| WO | WO-2017084004 | A1 * | 5/2017 | ........... A61N 5/1031 |
| WO | 2017133654 | A1 | 8/2017 | |
| WO | 2018090195 | A1 | 5/2018 | |

* cited by examiner

METHOD AND APPARATUS FOR CONTROLLING RADIOTHERAPY EQUIPMENT, DEVICE, AND STORAGE MEDIUM

CROSS-REFERENCE TO RELATED APPLICATION

This application is a U.S. national stage of international application No. PCT/CN2021/139698, filed on Dec. 20, 2021, the disclosure of which is herein incorporated by reference in its entirety.

TECHNICAL FIELD

The present disclosure relates to the technical field of medical instruments, and in particular to, relates a method and apparatus for controlling radiotherapy equipment, a device, and a storage medium.

BACKGROUND

In order to improve the treatment effect and the treatment efficiency of patients, radiotherapy equipment with double heads is adopted to carry out radiotherapy on patients. For the dual-head radiotherapy equipment, a plurality of treatment plans are provided for the same patient during treatment scheduling.

SUMMARY

Some embodiments of the present disclosure provide a method for controlling radiotherapy equipment that is configured to control a dual-head radiotherapy equipment, wherein the dual-head radiotherapy equipment includes a focused treatment head and a conformal treatment head, and the method includes:

acquiring a plurality of target treatment plans for a target object, wherein the plurality of target treatment plans include a treatment plan for the focused treatment head and a treatment plan for the conformal treatment head;

performing an examination on the plurality of target treatment plans; and controlling, in the case that the plurality of target treatment plans pass the examination, the focused treatment head to execute the treatment plan for the focused treatment head and the conformal treatment head to execute the treatment plan for the conformal treatment head.

In some embodiments, the acquiring the plurality of target treatment plans for the target object includes:

displaying a treatment plan list for the target object;

acquiring a plan-select operation input by a user, and identifying, based on the plan-select operation, the plurality of target treatment plans in the treatment plan list; and downloading, based on identifiers of the plurality of target treatment plans, the plurality of target treatment plans from corresponding storage positions.

In some embodiments, the performing the examination on the plurality of target treatment plans includes:

respectively performing an identifier examination of the target object and a treatment parameter examination on each of the plurality of target treatment plans;

determining, in the case that the target treatment plan passes both the identifier examination and the treatment parameter examination, that the target treatment plan passes the examination; and determining, in the case that the target treatment plan fails to pass at least one of the identifier examination or the treatment parameter examination, that the target treatment plan fails to pass the examination.

In some embodiments, the method further includes:

reacquiring, in the case that at least one of the plurality of target treatment plans fails to pass the examination, the plurality of target treatment plans, and examining the plurality of target treatment plans as reacquired.

In some embodiments, the method further includes:

acquiring, in the case that an interrupted treatment plan is present in any of the plurality of target treatment plans, a treatment record corresponding to the target treatment plan.

In some embodiments, the controlling the focused treatment head to execute the treatment plan for the focused treatment head and the conformal treatment head to execute the treatment plan for the conformal treatment head includes:

displaying the plurality of target treatment plans;

controlling the focused treatment head to execute the treatment plan for the focused treatment head and the conformal treatment head to execute the treatment plan for the conformal treatment head; and executing, in the case that a current target treatment plan is accomplished or interrupted, a next target treatment plan and displaying an accomplishment identifier of the current target treatment plan.

In some embodiments, the method further includes:

transmitting, in the case that an execution of the plurality of target treatment plans is accomplished, treatment records of the plurality of target treatment plans to an external storage device; wherein the execution of the target treatment plan being accomplished includes that: the target treatment plan is accomplished or the target treatment plan is interrupted.

Some embodiments of the present disclosure provide a computer device. The computer device includes a memory and a processor. The memory stores one or more computer programs executable by the processor, and the processor, when loading and running the one or more computer programs, is caused to perform the method for controlling the radiotherapy equipment according to the above embodiments.

Some embodiments of the present disclosure further provide a non-transitory storage medium. The storage medium stores one or more computer programs therein. The one or more computer programs, when loaded and run by a processor, cause the processor to perform the method for controlling the radiotherapy equipment according to the above embodiments.

BRIEF DESCRIPTION OF DRAWINGS

In order to more clearly illustrate the technical solutions in the embodiments of the present disclosure, the drawings required for the embodiments are briefly described below. It should be understood that the following drawings only illustrate some embodiments of the present disclosure and should not be considered as limiting the scope of the present disclosure, and other related drawings can be derived from these drawings by those of ordinary skill in the art without making creative efforts.

DETAILED DESCRIPTION

Figure 1:
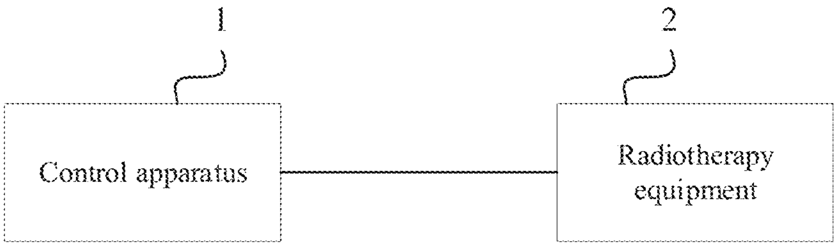
FIG. 1 is a schematic diagram of a system for controlling radiotherapy equipment according to some embodiments of the present disclosure.

For clearer descriptions of the objectives, technical solutions, and advantages of the embodiments of the present disclosure, the technical solutions in the embodiments of the present disclosure are clearly and completely described below with reference to the accompanying drawings of the embodiments of the present disclosure. Apparently, the described embodiments are merely some embodiments of the present disclosure, rather than all of the embodiments.

In the description of the present disclosure, it should be understood that directions or positional relationships indicated by the terms "center", "longitudinal", "transverse", "length", "width", "thickness", "upper", "lower", "front", "rear", "left", "right", "vertical", "horizontal", "top", "bottom", "inner", "outer", and the like are those shown based on the accompanying drawings, are merely intended to facilitate and simplify description rather than to indicate or imply that the indicated apparatus or element must have a specific direction and be structured and operated according to the specific direction, and should not be construed as limiting the present disclosure. In addition, the terms "first" and "second" are used for descriptive purposes only and are not to be construed as indicating or implying relative importance or to implicitly indicate the number of technical features indicated. Thus, features defined as "first", "second" etc., explicitly or implicitly include one or more of the features. In the description of the present disclosure, "plurality" refers to two or more, unless otherwise explicitly and specifically defined.

In the present disclosure, "exemplary" is used to mean "serving as an example, instance, or illustration". Any embodiment described herein as "exemplary" is not necessarily to be construed as preferred or advantageous over other embodiments. The following description is presented to enable any person skilled in the art to implement and use the present disclosure. In the following description, details are set forth for the purpose of explanation. It should be apparent to one of ordinary skill in the art that the present disclosure can also be implemented without these specific details. In other examples, well-known structures and processes are not set forth in detail in order to avoid obscuring the description of the present disclosure with unnecessary detail. Thus, the present disclosure is not intended to be limited to the embodiments shown but is to be accorded the widest scope consistent with the principles and features disclosed herein.

In some practices, although a plurality of treatment plans are scheduled for the same patient during the treatment schedule, only one treatment plan can be downloaded and executed at the same time for the control device in the actual practice.

Therefore, if a plurality of treatment plans are prepared for one patient, the control device needs to execute the downloading and executing process of the treatment plan again after downloading and executing one treatment plan, which makes the control process of the dual-head radiotherapy equipment more complicated, result in longer treatment cycle and delayed treatment time.

The method for controlling radiotherapy equipment according to the embodiments of the present disclosure achieves the control of the radiotherapy equipment based on treatment plans. Before the method for controlling radiotherapy equipment provided by the present disclosure is described, a system for controlling radiotherapy equipment applied in the embodiments of the present disclosure is illustrated with reference to the accompanying drawings. FIG. 1 is a schematic diagram of a system for controlling radiotherapy equipment according to some embodiments of the present disclosure. As shown in FIG. 1, the system for controlling radiotherapy equipment includes a control apparatus 1 and radiotherapy equipment 2. The control apparatus 1 is a device where a treatment control system (TCS) is located, and the control apparatus 1 is in communication connection with the radiotherapy equipment 2 to control the radiotherapy equipment 2. Specifically, the control apparatus 1 is connected with a motion controller of the radiotherapy equipment 2 through a radiotherapy control center. The radiotherapy control center is referred to as a radiation treatment center (RTC). The motion controller includes: a motion controller of a gantry, a motion controller of a treatment couch, and a motion controller of a treatment head, and the motion controller is, for example, in the product form of a programmable logic controller (PLC).

The radiotherapy equipment 2 is a single-head radiotherapy equipment or a dual-head radiotherapy equipment, and the control apparatus 1 controls the radiotherapy equipment by executing the method for controlling radiotherapy equipment provided in any one of the following embodiments. The single-head radiotherapy equipment is a focused treatment head or a conformal treatment head. The focused treatment head adopts cobalt 60 as a radiation source, or a particle accelerator as a radiation source. The conformal treatment head adopts cobalt 60 as a radiation source, or a particle accelerator as a radiation source. The dual-head radiotherapy equipment refers to radiotherapy equipment in which two treatment heads are arranged on the same roller, and in one example, the two treatment heads include a focused treatment head and a conformal treatment head, or two focused treatment heads, or two conformal treatment heads. The focused treatment head is, for example, a gamma knife treatment head, and the conformal treatment head is, for example, a medical accelerator treatment head.

Figure 2:
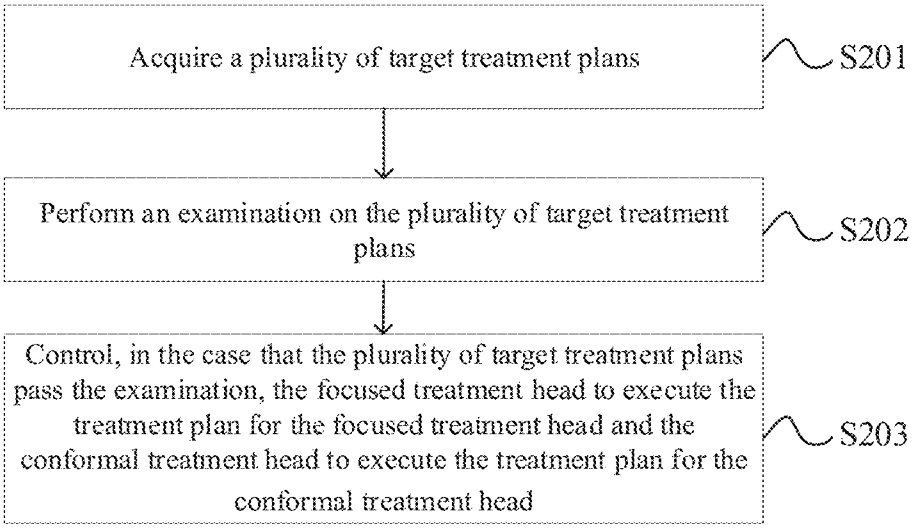
FIG. 2 is a schematic flowchart of a method for controlling radiotherapy equipment according to some embodiments of the present disclosure.

The method for controlling radiotherapy equipment provided by the present disclosure is illustrated by a plurality of embodiments with reference to the accompanying drawings as follows. FIG. 2 is a schematic flowchart of a method for controlling radiotherapy equipment according to some embodiments of the present disclosure, and as shown in FIG. 2, the method for controlling the radiotherapy equipment includes the following steps.

In S201, a plurality of target treatment plans are acquired.

The plurality of target treatment plans are treatment plans for the same target object and include a treatment plan for the focused treatment head and a treatment plan for the conformal treatment head.

The treatment plans, whether they are treatment plans for the focused treatment head or treatment plans for the conformal treatment head, include at least one treatment plan for the same target region of the same target object, or at least two treatment plans for different target regions of the same target object, or include at least one treatment plan for one target region of the same target object and at least one treatment plan for other different target regions of the same target object. That is, the plurality of target treatment plans are not limited to the regions for the target object, and are treatment plans for respective treatment heads for the same target object.

In some embodiments, the treatment plans for the focused treatment head are all treatment plans, or part of the treatment plans, for the same target object; the treatment plans for the conformal treatment head are also all treatment plans, or part of the treatment plans, for the conformal treatment head for the same target object.

In some embodiments, a plurality of target treatment plans are downloaded from a preset external storage position or are loaded from a local storage position. The external storage device is, for example, another device communicatively connected to the radiotherapy control apparatus, such as a cloud server, or a radiotherapy scheduling (OIS) device.

In S202, an examination on the plurality of target treatment plans is performed.

In order to ensure accurate execution of the target treatment plans in the case that the plurality of target treatment plans are acquired, a medical record examination is carried out on the plurality of target treatment plans before the target treatment plans are executed, so as to determine whether each target treatment plan satisfies a preset medical record condition.

In the case that one target treatment plan meets the preset medical record condition, it is determined that the target treatment plan passes the examination; otherwise, in the case that one target treatment plan does not meet the preset medical record condition, it is determined that the target treatment plan fails to pass the examination. The examination of the target treatment plan includes an identifier examination of a treatment object in the target treatment plan and a treatment parameter examination on the target treatment plan.

In S203, in the case that the plurality of target treatment plans pass the examination, the focused treatment head and the conformal treatment head are controlled to respectively execute the corresponding treatment plans in the plurality of target treatment plans.

In the case that the plurality of target treatment plans pass the examination, the focused treatment head is controlled to execute the treatment plan for the focused treatment head, and the conformal treatment head is controlled to execute the treatment plan for the conformal treatment head. In some embodiments, target point information in each target treatment plan is sent to the RTC, such that the RTC controls, based on the target point information, a motion controller of a treatment head corresponding to each target treatment plan in the dual-head radiotherapy equipment to perform motions such as positioning and/or rotation, thereby achieving control execution on the target treatment plan.

According to the method for controlling the radiotherapy equipment provided in the embodiments, a plurality of target treatment plans for the focused treatment head and the conformal treatment head of the dual-head radiotherapy equipment are acquired, the plurality of target treatment plans are all examined, and under the condition that the plurality of target treatment plans pass the examination, the focused treatment head and the conformal treatment head are controlled to respectively execute the corresponding treatment plans in the plurality of target treatment plans, such that the batch acquisition, examination and control execution of the plurality of treatment plans for the same target object are achieved, and the acquisition, the examination and the execution of the treatment plans do not need to be carried out one by one, thereby effectively simplifying the control process of the dual-head radiotherapy equipment, shortening the treatment control cycle of the dual-head radiotherapy equipment, saving the treatment cycle for the same target object, and also avoiding the need for repeated positioning of a plurality of treatment plans.

Figure 3:
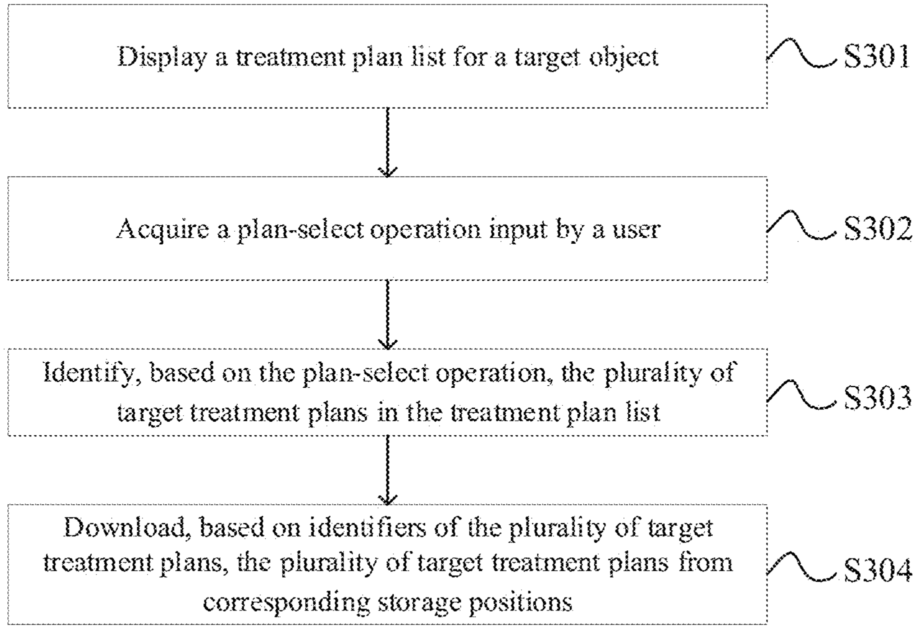
FIG. 3 is a schematic flowchart of acquiring target treatment plans in a method for controlling radiotherapy equipment according to some embodiments of the present disclosure.

On the basis of the method for controlling the radiotherapy equipment as described above, the embodiments of the present disclosure further provide a possible implementation example of the method for controlling the radiotherapy equipment. FIG. 3 is a schematic flowchart of acquiring target treatment plans in the method for controlling the radiotherapy equipment according to some embodiments of the present disclosure. As shown in FIG. 3, the acquiring the plurality of target treatment plans in S201 in the method as shown above includes the following steps.

In S301, a treatment plan list for the target object is displayed.

The radiotherapy control apparatus that executes the method for controlling the radiotherapy equipment is provided with a radiotherapy control interface, and the treatment plan list is displayed on the radiotherapy control interface. The treatment plan list includes unique identifiers of the plurality of treatment plans for the target object. For example, as the plurality of treatment plans for the target object have a certain execution order, unique identifiers of the plurality of treatment plans in the treatment plan list are sequentially displayed based on the execution order.

In S302, a plan-select operation input by a user is acquired.

The plan-select operation is, for example, a pick operation for the plurality of target treatment plans, wherein the pick operation is a check operation for each target treatment plan or a click-confirm operation.

In S303, the plurality of target treatment plans in the treatment plan list are identified based on the plan-select operation.

Under the condition of acquiring the plan-select operation, treatment plans picked by the plan-select operation are determined as a plurality of target treatment plans from the plurality of treatment plans in the treatment plan list, and the plurality of target treatment plans in the treatment plan list are identified to indicate that the plurality of target treatment plans are selected.

In S304, the plurality of target treatment plans are downloaded from corresponding storage positions based on identifiers of the plurality of target treatment plans.

Under the condition of identifying the plurality of target treatment plans based on the plan-select operation, the plurality of target treatment plans are downloaded one by one from the preset storage positions based on the identifiers of the plurality of target treatment plans. The identifier of each target treatment plan is a unique identifier of each target treatment plan. The preset storage position is, for example, an external storage device, such as a cloud server, or a radiotherapy scheduling (OIS) device, or another type of storage device.

Under the condition of acquiring the plurality of target treatment plans by downloading, the plurality of target treatment plans are stored in a local preset storage directory corresponding to the identifiers of the respective target treatment plans. In the subsequent application process, the target treatment plans are directly acquired from the preset storage directory without repeated downloading of the treatment plans.

In the process of controlling the dual-head radiotherapy equipment to execute the target treatment plan, the target treatment plan may fail to be executed due to device failures or manual stop of an operator, and the target treatment plan that fails to be executed is regarded as an interrupted treatment plan. The device failures include a failure of the gantry, or a failure of the corresponding treatment head, or a failure of the treatment couch, or other failures present in the machine of the dual-head radiotherapy equipment.

In view of this, in the case that the interrupted treatment plan, i.e., a treatment plan that has failed to be executed before, is present in the plurality of target treatment plans, this execution means that the interrupted treatment plan is resumed and continued to be executed, and therefore, the interrupted treatment plan is also called a resumption treatment plan. To ensure that the interrupted treatment plan of the plurality of target treatment plans is accurately executed, the treatment record for the interrupted treatment plan is also required. The treatment record characterizes the historical treatment progress of the interrupted treatment plan. In the process of executing the interrupted treatment plan, the steps not previously executed in the interrupted treatment plan may continue to be executed based on the historical treatment progress without re-executing the plan. For example, in the case that four control points are present in the interrupted treatment plan, it is determined that three control points have been previously executed based on the historical treatment progress, and therefore, this execution is carried out only for the last control point in the interrupted treatment plan.

In some embodiments, for an interrupted treatment plan in the plurality of target treatment plans, under the condition of acquiring the interrupted treatment plan from the external storage device, a treatment record of the interrupted treatment plan is also acquired from the external storage device and stored in a specified directory corresponding to an identifier of the interrupted treatment plan.

Figure 4:
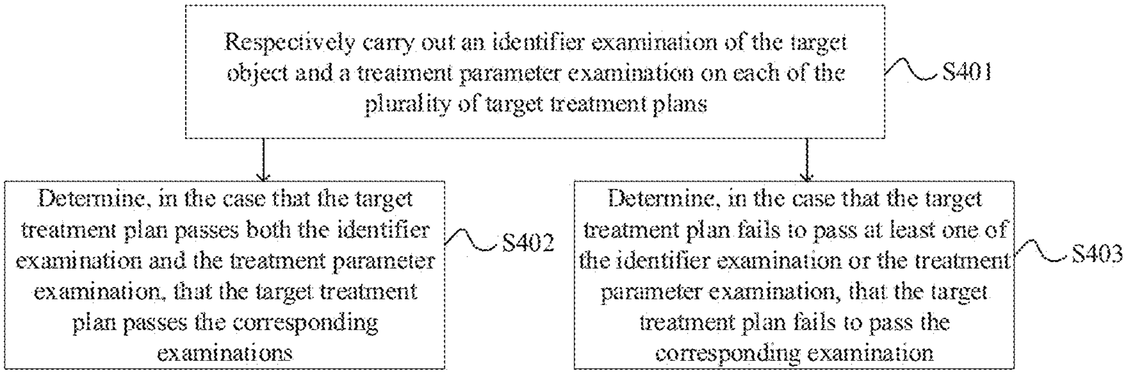
FIG. 4 is a schematic flowchart of verifying treatment plans in a method for controlling radiotherapy equipment according to some embodiment of the present disclosure.

On the basis of the method for controlling the radiotherapy equipment provided in any of the above embodiments, the embodiments of the present disclosure further provide examining treatment plans in the method for controlling the radiotherapy equipment. FIG. 4 is a schematic flowchart of examining treatment plans in the method for controlling the radiotherapy equipment according to some embodiment of the present disclosure. As shown in FIG. 4, the examining the plurality of target treatment plans in S202 in the method as shown above includes the following steps.

In S401, an identifier examination of the target object and a treatment parameter examination on the plurality of target treatment plans are carried out, respectively.

In some embodiments, the identifier examination of the target object is achieved in the following manner: carrying out the identifier examination on each target treatment plan based on the identifier of the target object to determine whether an object identifier corresponding to each target treatment plan is matched with the identifier of the target object, and in the case that the object identifier corresponding to each target treatment plan is matched with the identifier of the target object, determining that the treatment object for the target treatment plan is the target object, that is, the identifier of the target object passes the examination; otherwise, in the case that the object identifier corresponding to each target treatment plan is not matched with the identifier of the target object, determining that the treatment object for the target treatment plan is not the target object, that is, the identifier of the target object fails to pass the examination. For example, the identifier of the target object includes, for example, an identity identifier, such as the identification card number or the name or other information of the target object. Correspondingly, the object identifier corresponding to the target treatment plan also includes an identity identifier of the treatment object. In the process of carrying out the identifier examination of the target treatment plan, the identity identifier of the target object is compared with the identity identifier of the treatment object corresponding to the target treatment plan, and in the case that the two identity identifiers are identical, it is determined that the object identifier corresponding to the target treatment plan is matched with the identifier of the target object. Otherwise, in the case that the two identity identifiers are different, it is determined that the object identifier corresponding to the target treatment plan is not matched with the identifier of the target object.

In the method provided in the embodiments, the treatment object corresponding to the target treatment plan is ensured to be the target object of the current treatment by carrying out the identifier examination on the target treatment plan, thereby ensuring the accuracy of the treatment object, and avoiding incorrect execution of the treatment plan.

In some embodiments, the treatment parameter examination is achieved in the following manner: examining whether the treatment parameters in each target treatment plan are within a range of treatment parameters of the treatment head corresponding to the target treatment plan, and in the case that the treatment parameters in the target treatment plan are within the range of the treatment parameters of the corresponding treatment head, determining that the treatment parameters in the target treatment plan pass the examination; otherwise, in the case that the treatment parameters in the target treatment plan are not within the range of the treatment parameters of the corresponding treatment head, determining that the treatment parameters in the target treatment plan fail to pass the examination.

The treatment parameters include, for example, dosage parameters, and/or, roller rotation parameters, such as a rotational speed.

In some embodiments, the dosage parameters examination includes, for example, comparing the dosage parameters in each target treatment plan with a maximum dosage parameter of the treatment head corresponding to the target treatment plan, and in the case that the dosage parameters in the target treatment plan are greater than the maximum dosage parameter of the corresponding treatment head, determining that the dosage parameters in the target treatment plan are not within a range of dosage parameters of the corresponding treatment head, that is, the dosage parameters of the target treatment plan fail to pass the examination; otherwise, in the case that the dosage parameters in the target treatment plan are not greater than the maximum dosage parameter of the corresponding treatment head, determining that the dosage parameters of the target treatment plan are within the range of the dosage parameters of the corresponding treatment head, that is, the dosage parameters of the target treatment plan pass the examination.

In some embodiments, taking the roller rotation parameter as the roller rotational speed as an example, the roller rotational speed examination includes, for example, comparing a roller rotational speed in the target treatment plan with a maximum rotational speed of the roller, and in the case that the rotational speed in the target treatment plan is faster than the maximum rotational speed of the roller, determining that the roller rotational speed in the target treatment plan is not within a range of the rotational speed of the roller, that is, the roller rotation parameter in the target treatment plan fails to pass the examination; otherwise, in the case that the rotational speed in the target treatment plan is not faster than the maximum rotational speed of the roller, determining that the roller rotational speed in the target treatment plan is within the range of the rotational speed of the roller, that is, the roller rotation parameter of the target treatment plan passes the examination. In the method provided in the embodiments, the identifier examination of the target object and the treatment parameter examination in the plurality of target treatment plans are carried out, such that the target treatment plan is accurately executed by the corresponding treatment head of the dual-head radiotherapy equipment, thereby effectively avoiding the plan execution interruption caused by device failures in the execution of the target treatment plan due to the treatment parameters, and also ensuring the accurate and safe treatment on the treatment object as much as possible.

In S402, in the case that the target treatment plan passes both the identifier examination and the treatment parameter examination, it is determined that the target treatment plan passes the examination.

In S403, in the case that the target treatment plan fails to pass at least one of the identifier examination or the treatment parameter examination, it is determined that the target treatment plan fails to pass the examination.

It is determined that the target treatment plans pass the examination only when passing both the identifier examination and the treatment parameter examination; and it is determined that the target treatment plans fail to pass the examination as long as the target treatment plans fail to pass at least one of the identifier examination and the treatment parameter examination.

In the method provided in the embodiments, the target treatment plans are subjected to the identifier examination of the treatment object and the treatment parameter examination, and it is determined that the target treatment plans pass the examination only when passing both the two examinations, thereby ensuring safe and accurate execution of the target treatment plans, and ensuring the execution reliability of the target treatment plans.

On the basis of the method for controlling the radiotherapy equipment provided in any of the above embodiments, in the case that at least one of the plurality of target treatment plans fails to pass the examination, the method further includes:

reacquiring the plurality of target treatment plans and examining the plurality of target treatment plans.

That is to say, once at least one target treatment plan fails to pass the examination, the plurality of acquired target treatment plans are refused to be loaded, and the treatment plans that fail to pass the examination are adjusted and rescheduled until the respective adjusted treatment plans all pass the examination.

Figure 5:
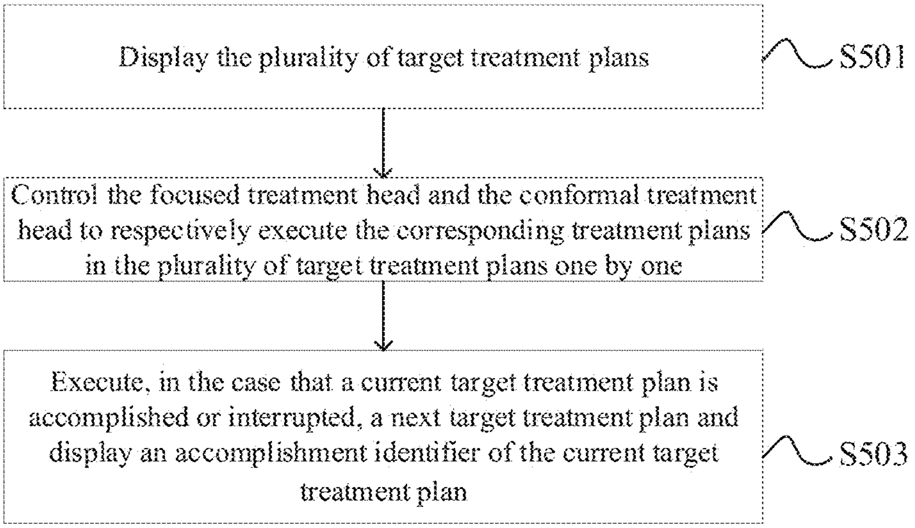
FIG. 5 is a schematic flowchart of executing treatment plans in a method for controlling radiotherapy equipment according to some embodiment of the present disclosure.

On the basis of the method for controlling the radiotherapy equipment provided in any of the above embodiments, the embodiments of the present disclosure are also illustrated based on a possible implementation example of the treatment plans in the execution process. FIG. 5 is a schematic flowchart of executing treatment plans in the method for controlling the radiotherapy equipment according to some embodiment of the present disclosure. As shown in FIG. 5, the controlling the focused treatment head and the conformal treatment head to respectively execute the corresponding treatment plans in the plurality of target treatment plans in S203 in the method as shown above includes the following steps.

In S501, the plurality of target treatment plans are displayed.

In some embodiments, identifiers of the plurality of target treatment plans, such as names of the plurality of target treatment plans, are displayed on the radiotherapy control interface.

In S502, the focused treatment head and the conformal treatment head are controlled to respectively execute the corresponding treatment plans in the plurality of target treatment plans one by one.

In S503, in the case that a current target treatment plan is accomplished or interrupted, a next target treatment plan is executed and an accomplishment identifier of the current target treatment plan is displayed.

In some embodiments, the plurality of target treatment plans are loaded in sequence based on a preset execution order of the plurality of target treatment plans. For the currently loaded target treatment plan, a treatment head corresponding to the currently loaded target treatment plan is controlled to execute the currently loaded target treatment plan, and in the case that the execution of the currently loaded target treatment plan is accomplished, that is, the treatment is completed or interrupted, the execution of a next target treatment plan proceeds and a treatment head corresponding to the next target execution plan is controlled to execute the next target execution plan.

In this case, an accomplishment identifier of the currently executed target treatment plan is also displayed on the radiotherapy control interface based on the execution condition of the currently executed target treatment plan. The accomplishment identifier indicates whether the currently executed target treatment plan is accomplished. The accomplishment identifier is a first identifier in the case that the currently executed target treatment plan is accomplished, and the accomplishment identifier is a second identifier in the case that the currently executed target execution plan is interrupted. The first identifier is, for example, a tick identifier, and the second identifier is, for example, a cross mark. In an actual application scenario, the first identifier and the second identifier are also identifiers in other forms, as long as they are two different identifiers.

It should be noted that, a user determines that the execution of the current target treatment plan is accomplished based on the accomplishment identifier displayed on the interface, and manually switches to execute the next target treatment plan; or the execution of the current target treatment plan is automatically switched to the execution of a next target execution plan under the condition of automatically detecting the execution of the current target treatment plan being accomplished.

In some embodiments, medical record information of the currently executed target treatment plan is displayed on a target point information interface, and after the target treatment plan is switched, the display content of the target point information interface is updated along with the switched target treatment plan so as to display the medical record information of the switched target treatment plan.

In the method for controlling the radiotherapy equipment provided in the embodiments of the present disclosure, the accurate execution of a plurality of target treatment plans is ensured by limiting the execution control process of the plurality of target treatment plans, and simultaneously, an accomplishment identifier of the current target treatment plan is displayed, such that a user can conveniently know the execution condition of the target treatment plan in time.

In some embodiments of the present disclosure, the method for controlling the radiotherapy equipment further includes:

transmitting, in the case that the execution of the plurality of target treatment plans is accomplished, treatment records of the plurality of target treatment plans to an external storage device.

In the step, the execution of the target treatment plan being accomplished includes that: the target treatment plan is accomplished or the target treatment plan is interrupted. That is, it is determined that the execution of the target treatment plan is accomplished as long as one target treatment plan is accomplished or interrupted. In the case that the execution of the plurality of target treatment plans is accomplished, the treatment records of the plurality of target treatment plans are transmitted to the external storage device for storage by calling a preset interface. The external storage device is, for example, a cloud server or a radiotherapy scheduling (OIS) device. The preset interface is a preset access interface of the external storage device. Subsequently, in the application process, a treatment record corresponding to a target treatment plan is also acquired from the external storage device via the preset interface.

The treatment record for each target treatment plan is a treatment record generated during the execution of the corresponding target treatment plan.

It should be noted that, in the case that a user knows that the execution of the plurality of target treatment plans is accomplished based on the accomplishment identifiers displayed on the radiotherapy control interface, the user manually triggers the transmission of the treatment records for the plurality of target treatment plans to the external storage device. The manual trigger is, for example, clicking a medical case closing button on the radiotherapy control interface for triggering. In other implementation examples, after it is automatically detected that the execution of the plurality of target treatment plans is accomplished, the transmission of the treatment records for the plurality of target treatment plans to the external storage device is triggered, which is not limited in the embodiments of the present disclosure.

In the method for controlling the radiotherapy equipment provided in the embodiments of the present disclosure, in the case that the execution of the plurality of target treatment plans is accomplished, the treatment records for the plurality of target treatment plans are transmitted to the external storage device at one time, thereby achieving the one-time return of the plurality of target treatment plans.

The following describes an apparatus, a device, and a storage medium for implementing the method for controlling the radiotherapy equipment provided by the present disclosure, and the specific implementation process and technical effects thereof are referred to above and are not described again below.

Figure 6:
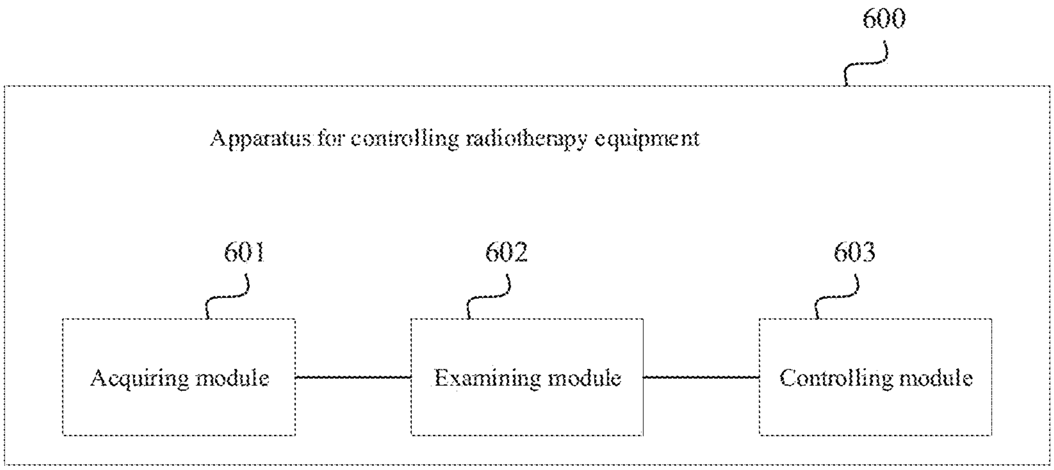
FIG. 6 is a schematic diagram of an apparatus for controlling radiotherapy equipment according to some embodiments of the present disclosure.

FIG. 6 is a schematic diagram of an apparatus for controlling radiotherapy equipment according to some embodiments of the present disclosure. The apparatus for controlling radiotherapy equipment provided in the embodiments of the present disclosure is configured to control dual-head radiotherapy equipment, and the dual-head radiotherapy equipment includes a focused treatment head and a conformal treatment head. As shown in FIG. 6, the apparatus 600 for controlling radiotherapy equipment includes:

an acquiring module 601, configured to acquire a plurality of target treatment plans for a target object, wherein the plurality of target treatment plans include: a treatment plan for the focused treatment head and a treatment plan for the conformal treatment head;

an examining module 602, configured to perform an examination on the plurality of the target treatment plans; and a controlling module 603, configured to control, in the case that the plurality of target treatment plans pass the examination, the focused treatment head to execute the treatment plan for the focused treatment head and the conformal treatment head to execute the treatment plan for the conformal treatment head.

In some embodiments, the acquiring module 601 includes:

a first display unit, configured to display a treatment plan list for the target object;

an identifying unit, configured to acquire a plan-select operation input by a user, and identify, based on the plan-select operation, the plurality of target treatment plans in the treatment plan list; and a downloading unit, configured to download, based on identifiers of the plurality of target treatment plans, the plurality of target treatment plans from corresponding storage positions.

In some embodiments, the examining module 602 is specifically configured to respectively perform an identifier examination of the target object and a treatment parameter examination on each of the plurality of target treatment plans; determine, in the case that the target treatment plan passes both the identifier examination and the treatment parameter examination, that the target treatment plan passes the examination; and determine, in the case that the target treatment plan fails to pass at least one of the identifier examination or the treatment parameter examination, that the target treatment plan fails to pass the examination.

In some embodiments, the acquiring module 601 is further configured to reacquire, in the case that at least one of the plurality of target treatment plans fails to pass the examination, the plurality of target treatment plans; and the examining module 602 is further configured to examine the plurality of reacquired target treatment plans as reacquired.

In some embodiments, the acquiring module 601 is further configured to acquire, in the case that an interrupted treatment plan is present in any of the plurality of target treatment plans, a treatment record corresponding to the target treatment plan.

In some embodiments, the controlling module 603 includes:

a second display unit, configured to display the plurality of target treatment plans;

a control unit, configured to control the focused treatment head to execute the treatment plan for the focused treatment head and the conformal treatment head to execute the treatment plan for the conformal treatment head; and execute, in the case that a current target treatment plan is accomplished or interrupted, a next target treatment plan; and the second display unit, further configured to display an accomplishment identifier of the current target treatment plan.

In some embodiments, the apparatus 600 for controlling radiotherapy equipment further includes:

a transmitting module, configured to transmit, in the case that an execution of the plurality of target treatment plans is accomplished, treatment records of the plurality of target treatment plans to an external storage device; and the execution of the target treatment plan being accomplished includes that: the target treatment plan is accomplished or the target treatment plan is interrupted.

The apparatus described above is configured to implement the method for controlling the radiotherapy equipment provided in the aforementioned embodiments, and the implementation principle and technical effects are similar, which are not described herein again.

The above modules are one or more integrated circuits configured to implement the above method, such as, one or more application-specific integrated circuits (ASICs), or one or more digital signal processors (DSPs), or one or more field programmable gate arrays (FPGAs). For another example, in the case that one of the above modules is implemented in the form of scheduling program codes for a processing element, the processing element is a general-purpose processor, such as a central processing unit (CPU) or other processors capable of calling program codes. For another example, these modules are integrated together and implemented in the form of a system-on-a-chip (SOC).

Figure 7:
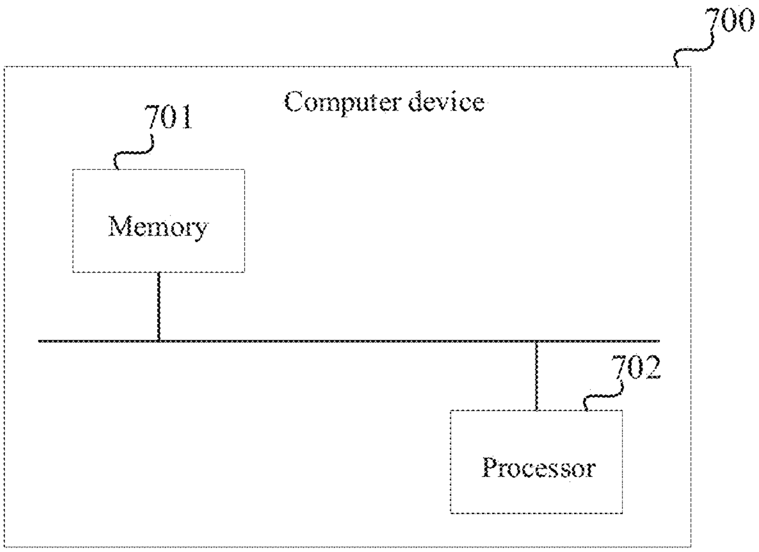
FIG. 7 is a schematic diagram of a computer device according to some embodiments of the present disclosure.

FIG. 7 is a schematic diagram of a computer device according to some embodiments of the present disclosure. The computer device is integrated into an apparatus or a chip of the apparatus, and the computer device is provided with a computing processing function, which is a treatment control device communicatively connected to radiotherapy equipment, such as a TCS device.

The computer device 700 includes a memory 701 and a processor 702. The memory 701 and the processor 702 are connected via a bus.

The memory 701 stores one or more computer programs executable by the processor 702, and the processor 702, when loading and running the one or more computer programs, is caused to implement the above method embodiments. The specific implementation and technical effects are similar, and are not described herein again.

On the basis of the method for controlling the radiotherapy equipment described above, the embodiments of the present disclosure further provide a computer-readable storage medium configured to implement the method for controlling the radiotherapy equipment, which is a non-transitory storage medium storing one or more computer programs. The one or more computer programs, when loaded and run by a processor, cause the processor to perform the above method embodiments.

In the several embodiments provided in the present disclosure, it should be understood that the disclosed apparatus and method may be implemented in other manners. For example, the above-described apparatus embodiments are merely illustrative. For example, the division of the units is only one type of logical functional division, and other divisions may be achieved in practice. For example, a plurality of units or components may be combined or integrated into another system, or some features may be omitted, or not executed. In addition, the shown or discussed mutual coupling or direct coupling or communication connection may be an indirect coupling or communication connection through some interfaces, apparatuses, or units, and may be in an electrical, mechanical, or another form.

The units described as separate parts may or may not be physically separate, and parts displayed as units may or may not be physical units, may be located in one location, or may be distributed on a plurality of network units. Some or all of the units can be selected according to actual needs to achieve the purpose of the solutions of the embodiments.

In addition, various functional units in the embodiments of the present disclosure may be integrated into one processing unit, or various units may be physically present separately, or two or more units may be integrated into one unit. The integrated unit may be implemented in the form of hardware, or in the form of hardware plus software functional unit.

The integrated unit implemented in the form of a software functional unit may be stored in a computer-readable storage medium. The software functional unit is stored in a storage medium and includes several instructions to enable a computer device (which may be a personal computer, a server, or a network device) or a processor to execute some steps of the method according to the embodiments of the present disclosure. The aforementioned storage media include various media capable of storing program codes, such as a U-disk, a mobile hard disk, a read-only memory (ROM), a random access memory (RAM), a magnetic disk, and an optical disk.

The above descriptions are only specific embodiments of the present disclosure, but the protection scope of the present disclosure is not limited to these. Any technical personnel skilled in the art can easily think of changes or substitutions within the technical scope disclosed herein, and these changes or substitutions shall fall within the protection scope of the present disclosure. Therefore, the protection scope of the present disclosure shall be subject to the protection scope of the claims.

The invention claimed is:

1. A method for controlling radiotherapy equipment, applicable to control dual-head radiotherapy equipment comprising a focused treatment head and a conformal treatment head, the method comprises:

acquiring a plurality of target treatment plans for a target object, wherein the plurality of target treatment plans comprise a treatment plan for the focused treatment head and a treatment plan for the conformal treatment head;

performing an examination on the plurality of target treatment plans;

controlling, in a case that the plurality of target treatment plans pass the examination, the focused treatment head to execute the treatment plan for the focused treatment head and the conformal treatment head to execute the treatment plan for the conformal treatment head; and transmitting, in a case that an execution of the plurality of target treatment plans is accomplished, treatment records of the plurality of target treatment plans to an external storage device; wherein the execution of the plurality of target treatment plans being accomplished comprises that one of the plurality of target treatment plans is accomplished or the one of the plurality of target treatment plans is interrupted.

2. The method according to claim 1, wherein the acquiring the plurality of target treatment plans for the target object comprises:

displaying a treatment plan list for the target object on a radiotherapy control interface;

acquiring a plan-select operation input by a user, and identifying, based on the plan-select operation, the plurality of target treatment plans in the treatment plan list; and downloading, based on identifiers of the plurality of target treatment plans, the plurality of target treatment plans from corresponding storage positions.

3. The method according to claim 1, wherein the performing the examination on the plurality of target treatment plans comprises:

respectively performing an identifier examination of the target object and a treatment parameter examination on each of the plurality of target treatment plans;

determining, in a case that a respective target treatment plan passes both the identifier examination and the treatment parameter examination, that the respective target treatment plan passes the examination; and determining, in a case that the respective target treatment plan fails to pass at least one of the identifier examination or the treatment parameter examination, that the respective target treatment plan fails to pass the examination.

4. The method according to claim 1, further comprising:

reacquiring, in a case that at least one of the plurality of target treatment plans fails to pass the examination, the plurality of target treatment plans, and examining the plurality of target treatment plans as reacquired.

5. The method according to claim 1, further comprising:

acquiring, in a case that an interrupted treatment plan is present in any of the plurality of target treatment plans, a treatment record corresponding to the interrupted treatment plan.

6. The method according to claim 1, wherein the controlling the focused treatment head to execute the treatment plan for the focused treatment head and the conformal treatment head to execute the treatment plan for the conformal treatment head comprises:

displaying the plurality of target treatment plans on a radiotherapy control interface;

controlling the focused treatment head to execute the treatment plan for the focused treatment head and the conformal treatment head to execute the treatment plan for the conformal treatment head; and executing, in a case that a current target treatment plan is accomplished or interrupted, a next target treatment plan and displaying an accomplishment identifier of the current target treatment plan.

7. A non-transitory computer-readable storage medium storing one or more computer programs therein, wherein the one or more computer programs, when loaded and run by a processor, cause the processor to perform:

acquiring a plurality of target treatment plans for a target object, wherein the plurality of target treatment plans comprise a treatment plan for a focused treatment head and a treatment plan for a conformal treatment head;

performing an examination on the plurality of target treatment plans; controlling, in a case that the plurality of target treatment plans pass the examination, the focused treatment head to execute the treatment plan for the focused treatment head and the conformal treatment head to execute the treatment plan for the conformal treatment head; and transmitting, in a case that an execution of the plurality of target treatment plans is accomplished, treatment records of the plurality of target treatment plans to an external storage device; wherein the execution of the plurality of target treatment plans being accomplished comprises that one of the plurality of target treatment plans is accomplished or the one of the plurality of target treatment plans is interrupted.

8. The computer-readable storage medium according to claim 7, wherein the one or more computer programs, when loaded and run by the processor, cause the processor to perform:

displaying a treatment plan list for the target object on a radiotherapy control interface;

acquiring a plan-select operation input by a user, and identifying, based on the plan-select operation, the plurality of target treatment plans in the treatment plan list; and downloading, based on identifiers of the plurality of target treatment plans, the plurality of target treatment plans from corresponding storage positions.

9. The computer-readable storage medium according to claim 7, wherein the one or more computer programs, when loaded and run by the processor, cause the processor to perform:

respectively performing an identifier examination of the target object and a treatment parameter examination on each of the plurality of target treatment plans;

determining, in a case that a respective target treatment plan passes both the identifier examination and the treatment parameter examination, that the respective target treatment plan passes the examination; and determining, in a case that the respective target treatment plan fails to pass at least one of the identifier examination or the treatment parameter examination, that the respective target treatment plan fails to pass the examination.

10. The computer-readable storage medium according to claim 7, wherein the one or more computer programs, when loaded and run by the processor, cause the processor to perform:

reacquiring, in a case that at least one of the plurality of target treatment plans fails to pass the examination, the plurality of target treatment plans, and examining the plurality of target treatment plans as reacquired.

11. The computer-readable storage medium according to claim 7, wherein the one or more computer programs, when loaded and run by the processor, cause the processor to perform:

acquiring, in a case that an interrupted treatment plan is present in any of the plurality of target treatment plans, a treatment record corresponding to the interrupted treatment plan.

12. The computer-readable storage medium according to claim 7, wherein the one or more computer programs, when loaded and run by the processor, cause the processor to perform:

displaying the plurality of target treatment plans on a radiotherapy control interface;

controlling the focused treatment head to execute the treatment plan for the focused treatment head and the conformal treatment head to execute the treatment plan for the conformal treatment head; and executing, in a case that a current target treatment plan is accomplished or interrupted, a next target treatment plan and displaying an accomplishment identifier of the current target treatment plan.

13. A computer device, comprising: a memory and a processor, wherein the memory stores one or more computer programs executable by the processor, and the processor, when loading and running the one or more computer programs, is caused to perform:

acquiring a plurality of target treatment plans for a target object, wherein the plurality of target treatment plans comprise a treatment plan for a focused treatment head and a treatment plan for a conformal treatment head;

performing an examination on the plurality of target treatment plans;

controlling, in a case that the plurality of target treatment plans pass the examination, the focused treatment head to execute the treatment plan for the focused treatment head and the conformal treatment head to execute the treatment plan for the conformal treatment head; and transmitting, in a case that an execution of the plurality of target treatment plans is accomplished, treatment records of the plurality of target treatment plans to an external storage device; wherein the execution of the plurality of target treatment plans being accomplished comprises that one of the plurality of target treatment plans is accomplished or the one of the plurality of target treatment plans is interrupted.

14. The computer device according to claim 13, wherein the processor, when loading and running the one or more computer programs, is caused to perform:

displaying a treatment plan list for the target object on a radiotherapy control interface;

acquiring a plan-select operation input by a user, and identifying, based on the plan-select operation, the plurality of target treatment plans in the treatment plan list; and downloading, based on identifiers of the plurality of target treatment plans, the plurality of target treatment plans from corresponding storage positions.

15. The computer device according to claim 13, wherein the processor, when loading and running the one or more computer programs, is caused to perform:

respectively performing an identifier examination of the target object and a treatment parameter examination on each of the plurality of target treatment plans;

determining, in a case that a respective target treatment plan passes both the identifier examination and the treatment parameter examination, that the respective target treatment plan passes the examination; and determining, in a case that the respective target treatment plan fails to pass at least one of the identifier examination or the treatment parameter examination, that the respective target treatment plan fails to pass the examination.

16. The computer device according to claim 13, wherein the processor, when loading and running the one or more computer programs, is caused to perform:

reacquiring, in a case that at least one of the plurality of target treatment plans fails to pass the examination, the plurality of target treatment plans, and examining the plurality of target treatment plans as reacquired.

17. The computer device according to claim 13, wherein the processor, when loading and running the one or more computer programs, is caused to perform:

acquiring, in a case that an interrupted treatment plan is present in any of the plurality of target treatment plans, a treatment record corresponding to the interrupted treatment plan.

18. The computer device according to claim 13, wherein the processor, when loading and running the one or more computer programs, is caused to perform:

displaying the plurality of target treatment plans on a radiotherapy control interface;

controlling the focused treatment head to execute the treatment plan for the focused treatment head and the conformal treatment head to execute the treatment plan for the conformal treatment head; and executing, in a case that a current target treatment plan is accomplished or interrupted, a next target treatment plan and displaying an accomplishment identifier of the current target treatment plan.

* * * * *